United States Patent [19]

Heil

[11] Patent Number: 5,040,980

[45] Date of Patent: Aug. 20, 1991

[54] DENTAL HANDPIECE WITH SPRING GRIP CHUCK AND LEVER RELEASE MECHANISM

[75] Inventor: Donald J. Heil, Lake Villa, Ill.

[73] Assignee: Midwest Dental Products Corporation, Des Plaines, Ill.

[21] Appl. No.: 528,433

[22] Filed: May 25, 1990

Related U.S. Application Data

[63] Continuation-in-part of Ser. No. 361,569, Jun. 5, 1989, abandoned.

[51] Int. Cl.$^5$ .............................................. A61C 1/14
[52] U.S. Cl. ................................................... 433/127
[58] Field of Search .............. 433/127, 128, 129, 126, 433/147

[56] References Cited

U.S. PATENT DOCUMENTS

| | | | |
|---|---|---|---|
| 4,089,115 | 5/1978 | Heil et al. | 433/124 |
| 4,370,132 | 1/1983 | Wohlgemuth | 433/128 |
| 4,493,645 | 1/1985 | Nakanishi | 433/127 |
| 4,536,157 | 8/1985 | Maizenberg | 433/129 |
| 4,575,338 | 3/1986 | Maizenberg | 433/126 |
| 4,874,314 | 10/1989 | Fleer et al. | 433/129 |

FOREIGN PATENT DOCUMENTS

| | | |
|---|---|---|
| 3402635 | 8/1985 | Fed. Rep. of Germany . |
| 2555042 | 5/1985 | France . |
| 125303 | 6/1949 | Sweden . |

Primary Examiner—John G. Weiss
Assistant Examiner—Michael Lynch
Attorney, Agent, or Firm—Tilton, Fallon, Lungmus

[57] ABSTRACT

A dental handpiece having a bur-receiving chuck with spring jaws which exert a strong clamping force on the shank of a bur for operatively securing the bur to the handpiece rotor, such handpiece also having a lever-actuated bur release mechanism for forcing the jaws apart when removal and replacement of a bur is desired. A force-multiplying control lever for camming open the clamping jaws is an integrated part of the handpiece assembly and is carried by a removable disk-shaped cover that may be rotated with respect to the head of the handpiece to position the lever at whatever radial direction the user prefers. A helical cup spring frictionally engages the cover to maintain the lever in its selected direction of operation, and at least one annular leaf spring bears against a cam portion of the control lever to hold the lever in a retracted or lowered position during operation of the handpiece.

29 Claims, 3 Drawing Sheets

DENTAL HANDPIECE WITH SPRING GRIP CHUCK AND LEVER RELEASE MECHANISM

RELATED APPLICATION

This application is a continuation-in-part of co-pending application Ser. No. 361,569, filed June 5, 1989, now abandoned.

BACKGROUND

The chucks commonly used in high speed dental handpieces for releasably holding dental burs in place have chucking actions that can be generally categorized as falling within one of two groups. The first group includes wrench-operated chucks in which wrenches are utilized either to exert pushing or pulling forces to tighten such chucks. The second group includes spring grip chucks in which the bur-retaining force is generated by the spring action of the chuck and in which a wrench or some other means is utilized to open the jaws when bur removal or insertion is desired.

West German Patent DE 34 02 635 discloses a dental handpiece having a chuck with spring jaws that exert a gripping force on a dental bur. The jaws may be shifted into bur-releasing positions by depression of a push button at the upper end of the handpiece head. When the button is depressed, a wedge element is urged between the jaws to spread them apart and release the bur. However, field experiences with such a construction reveal operational problems that, until the present invention, have defied effective solution.

Bur slippage during handpiece operation is one such problem. Should such slippage occur, that is, should there be differences in the rotational speeds of a chuck and bur, the gripping jaws of such a chuck tend to wear rapidly, particularly in view of the high rotational speeds attained by modern high-speed handpieces (300,000 rpm or more). If such wear of the jaws, the bur, or both, is severe—and such a stage of wear may develop quickly—then there may be a significant risk of the bur releasing from the chuck while the turbine rotor continues to rotate at high speed. Recent efforts to reduce such slippage problems and their attendant risks have included providing the jaws of such a chuck with hardened metal tips; however, tempering or otherwise hardening the tips of such jaws is believed to be relatively expensive and of only limited effectiveness in reducing the slippage problem.

Another problem characterizing the type of chucking mechanism disclosed in the aforementioned German patent is the difficulty of opening the jaws of the chuck when bur release or insertion is desired. The spring jaws should grip a bur with sufficient force to avoid slippage, but efforts to generate such gripping forces have resulted in handpiece constructions which make it difficult if not impossible for an operator to apply sufficient force to the push button to cause bur release. In actual practice, dentists utilizing a handpiece of the type depicted in the patent commonly invert such a handpiece to press its release button forceably against a table surface or some other relatively immovable surface when bur removal or replacement is required.

In the past, the gripping force exerted by a chuck, whether of the wrench type or spring type, has often been determined by measuring the pull-out force needed to axially extract a bur from the jaws of a handpiece while the turbine is at rest. If the static pull-out forces are relatively high, it has been assumed that under dynamic conditions the releasing or slipping forces will also be relatively high. One aspect of this invention now lies in the discovery that such a correlation may not exist.

Other patents illustrating the state of the art are U.S. Pat. Nos. 4,536,157, 4,575,338, and 4,089,115.

SUMMARY OF THE INVENTION

The handpiece of this invention has a spring grip chuck that is notably effective in resisting rotational bur slippage during cutting and yet requires relatively little effort to operate when the jaws of the chuck must be opened for bur removal or insertion. Ease and convenience of chuck operation are thus attained without sacrificing gripping effectiveness and without special hardening or similar treatment of the tips of the jaws in an effort to prevent bur slippage.

Briefly, the handpiece of this invention includes a tubular spring metal chuck having its lower end portion secured within the bur tube or rotor tube of the handpiece and having at least a pair of bur-gripping jaws at its upper end. Even though the inwardly-directed forces exerted by the jaws against the shank of a bur are substantial, the spring jaws may be easily flexed outwardly into releasing positions by means of a pivotal control lever carried by a rotatable and removable disk-shaped cover at the upper end of the handpiece's head. When the handle portion of the lever is pivoted upwardly, an arcuate camming portion of the lever swings downwardly to drive a wedging element between the jaws of the chuck, thereby forcing the jaws into their opened positions. When fully raised or extended, the lever is pivoted beyond center so that the forces exerted by the spring jaws are transmitted by the wedging element back to the lever and serve to hold the lever in extended position until such time as the lever is again lowered or retracted by the operator. In its lowered position, the lever extends radially, but the direction of such radial extension may be adjusted over a full sweep of 360° to suit the needs and preferences of the operator. A helical cup spring exerts a constant restraining force against the disk-shaped cover to maintain the lever in its selected radially-directed position of adjustment.

When the jaws of the chuck are fully relaxed or untensioned, their arcuate inner surfaces or edges define arcuate segments of an opening substantially smaller in diameter than the shank of a bur intended to be clamped by such jaws. However, during manufacturing assembly, the jaws are flexed outwardly and "preset" in a tensioned, partially-opened condition with their edges spaced apart only slightly less than the minimum diameter of a standard bur shank. The result is that even when a bur of relatively small diameter (but within the standard range of 0.0626 to 0.0630 inches) is clamped by the jaws, the total jaw flexure (measured from fully relaxed or untensioned positions), and hence the gripping forces exerted by those jaws, are relatively great. Such radially-directed gripping forces, when applied through point contact by the jaws against the shank of a standard bur, have been found highly effective in preventing or resisting rotational slippage during cutting. Surprisingly, the high slip resisting action of the jaws does not appear to correlate with unusually high pull-out forces, it being discovered that pull-out resistance under static conditions is not a reliable gauge of slip resistance during a cutting operation.

The lower end portion of the chuck and the chuck-releasing wedge element, or at least the upper portion of that element, both have bores only slightly greater in diameter than the diameter of a standard bur shank, the differential being just great enough to facilitate insertion and extraction of a bur without producing looseness, vibration, or non-concentricity when a bur is clamped in place. In an alternative embodiment of the invention, the wedge element may be formed in two separate coaxial sections, the lower section with the wedging surfaces having an inside diameter sufficiently larger than the diameter of the upper section, and the diameter of a bur shank, to permit limited floating action of the lower section within the bur tube. Because of such limited floating action, the lower section is free to action of the lower section within the bur tube. Because of such limited floating action, the lower section is free to tip slightly, or become laterally displaced, upon forceful engagement with the chuck (when the jaws of the chuck are to be wedged into open positions) without affecting the axial alignment and piloting function of the upper section and the chuck's lower portion. Similarly, the chuck may effectively be formed in two coaxial sections with the lower section performing the piloting and chuck-presetting functions and the upper section performing the clamping function.

The control lever includes a handle portion and a relatively short cam portion, the two portions extending in opposite directions from the lever's transverse pivot axis. At least one annular leaf spring bears upwardly against the cam portion when the lever is in its normal lowered position to prevent unintended pivotal movement of the lever into raised position when the handpiece is in use. In a preferred embodiment, the cam portion includes a centrally-disposed arcuate camming surface engagable with the bearing surface of the chuck-releasing wedge element and a pair of arcuate contact surfaces on opposite sides of the arcuate camming surface, the latter being substantially closer to the transverse pivot axis than such camming surface, for engagement by the annular leaf spring means supported by the head. The disk-shaped cover includes a radial recess in which the operating lever is disposed when that lever is in its lowered or retracted condition. When the lever is raised, or partially raised, the ends of a C-shaped retaining spring may be exposed in said recess and urged together by a suitable tool to retract the retaining spring from an annular channel within the head and release the disk-shaped cover for removal from the head.

Other features, advantages, and objects will become apparent from the specification and drawings.

DETAILED DESCRIPTION OF PREFERRED EMBODIMENTS

Referring to the embodiment depicted in FIGS. 1–6, the numeral 10 generally designates a handpiece having a handle 11 and head 12. Within the chamber 13 of the head is a rotor 14 adapted to be driven by air under pressure supplied through handle 11. The rotor is supported for rotation by upper and lower bearing assemblies 15 and 16. Although of little importance for purposes of understanding the invention, resilient rings 17 and 18 support the bearing assemblies within chamber 13 for purposes of reducing noise levels and attenuating vibrations during handpiece operation.

Rotor 14 includes a bur tube or rotor tube 19, the bur tube having an axial bore 19a and open upper and lower ends 19b and 19c, respectively. The lower end 19c projects into an opening 12a at the lower end of handpiece head 12.

Within the lower portion of the bore 19a of the bur tube is a tubular spring metal chuck 20. The chuck has an open-ended axial bore 21 for receiving the cylindrical shank of a dental bur 22. The bur is conventional, having a standard Type III shank as specified in ISO (International Organization for Standardization) standard 1797-1985(E). In accordance with that standard, such a shank should have a diameter within the range of 0.0626 to 0.0630 inches.

Figures 1, 2, 3:
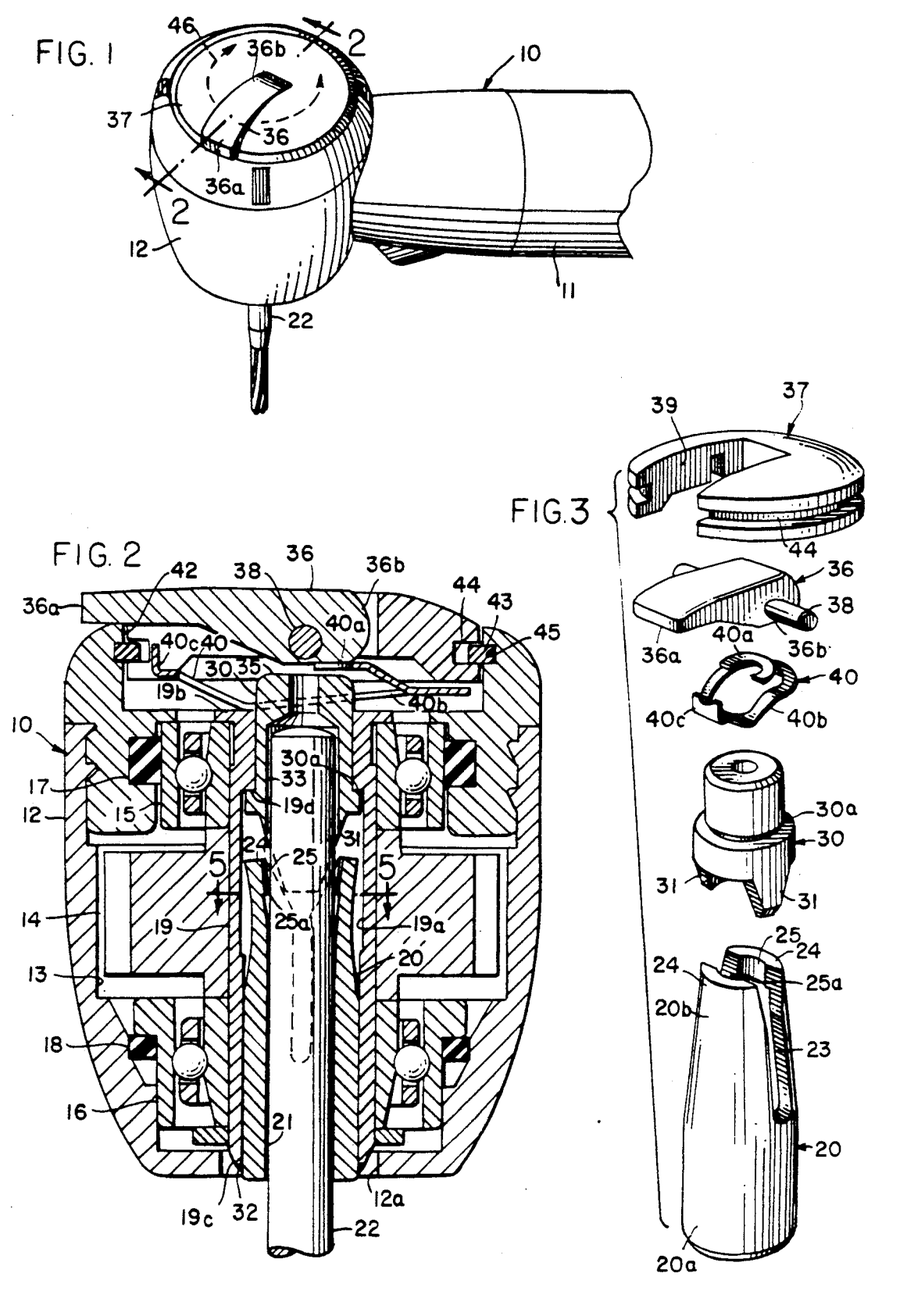
FIG. 1 is a perspective view of the head end portion of a dental handpiece embodying the chucking system of the present invention.
FIG. 2 is an enlarged vertical sectional view taken along line 2—2 of FIG. 1.
FIG. 3 is an exploded perspective view of the major components of the chucking system.
Figure 6:
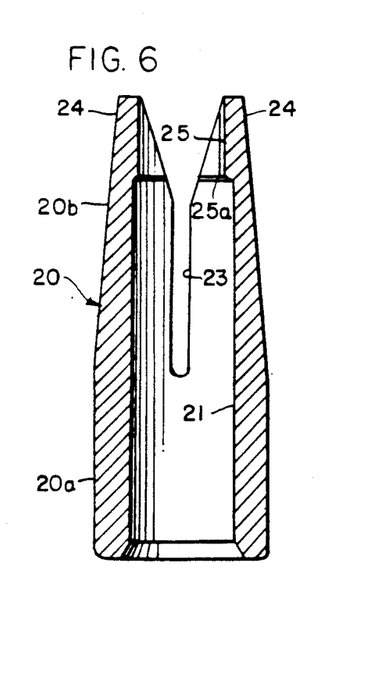
FIG. 6 is a longitudinal sectional view of the spring grip chuck in an untensioned state.

As shown most clearly in FIGS. 3 and 6, the spring grip chuck has a cylindrical lower end portion 20a and a tapered upper end portion 20b. The upper end portion is longitudinally slotted at 23 to provide at least two upwardly-extending bur-gripping jaws 24. The optimum number of such jaws is believed to be two; however, a greater number may be provided if desired. Such jaws are in any case provided at their upper ends with interior shoulder portions 25 having arcuate inner surfaces constituting segments of a bore of reduced diameter. Specifically, the opening defined by such surfaces at the time of chuck manufacture should have a diameter within the range of about 0.050 to 0.058 inches if the chuck is designed to receive standard burs of the 0.0626 to 0.0630 size range. The preferred diameter of the opening defined by interior shoulder portions 25 is believed to be about 0.052 to 0.056 inches with particularly effective results being obtained with a diameter of 0.053 to 0.055 inches.

Figure 5:
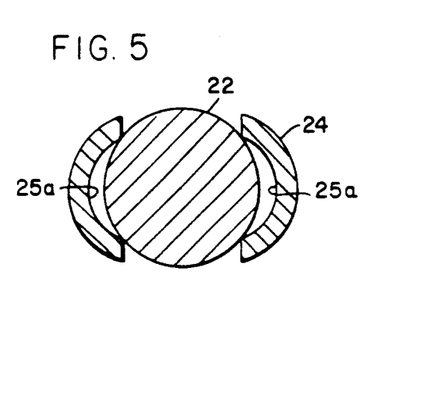
FIG. 5 is a greatly enlarged and somewhat exaggerated cross sectional view taken along line 5—5 of FIG. 2.

It is to be emphasized that the specified diameter for the opening defined by the opposing surfaces of shoulder portions 25 is determined at the time of manufacture when the spring chuck is in an untensioned state. When the chuck is in use, with a bur 22 gripped by the jaws 24, the jaws are flexed outwardly as depicted most clearly in FIG. 2. Under such conditions, only the lower edges 25a of shoulder portions 25 engage the cylindrical surface of the bur shank and, more specifically, only the corners or ends of such edges contact the bur shank because of the greater radius of curvature of the shank in relation to the radius of curvature of each of the lower edges 25a. Thus, as shown in FIG. 5, edges 25a engage the shank at four circumferentially-spaced points of contact. Such a relationship assumes perfect concentricity between the bur shank and the chuck; if perfect concentricity is not attained, then such contact may occur at only three points (with an end or corner of one of the edges 25a being out of contact with the shank). It is also to be understood that if a greater number of jaws are provided, a correspondingly greater number of contact points will be made.

Chuck releasing means in the form of a generally cylindrical wedge-providing element 30 is slidably received in the upper end 19a of bur tube 19. Annular shoulders 30a and 19d are provided by element 30 and bur tube 19, respectively, for limiting the extent of upward sliding movement of that element or member. At its lower end, the chuck releasing element or member is provided with wedge portions 31 that project into slots 23 of the chuck 20.

To prevent free sliding movement of element 30, the parts are preset during assembly so that the spring jaws 24 of the chuck are held in partially outwardly-flexed condition by wedge portions 31 even when the jaws are in their "closed" positions without a bur retained thereby. An important additional effect is that such jaws are already in a tensioned state prior to being opened for bur insertion or, stated differently, are preset to exert substantial clamping force on a bur having only slightly greater diameter than the diameter of the opening between the jaws when such jaws are closed without a bur clamped therebetween. Because the jaws of the chuck are pretensioned to exert substantial gripping force, and because further outward flexure increases both their tension and gripping force, such a chuck is highly effective in holding burs against rotational slippage during handpiece operation.

While such a construction does not appear to result in a relationship in which the bur pull-out forces are notably greater than, or even exceed, the pull-out forces for other spring grip chucks that are commercially available, the construction of this invention is particularly resistant to bur slippage (relative rotation between bur and chuck) during cutting operations. Such results are attained without hardening or special treatment of the tips of jaws 24. The preset condition is achieved by first inserting the wedge element or member 30 into its fully raised position within the bore 19a of bur tube 19, then inserting chuck 20 until its jaws engage wedge portions 31 and flex outwardly to a limited extent, and finally permanently securing the chuck in position by weld 32 at the lower ends of the chuck and bur tube (FIG. 2).

The pretensioning of the jaws should be substantial enough so that the difference in jaw spacing when in untensioned condition (before presetting) and when engaging a bur of minimum diameter (0.0626 inches) is about 0.005 to 0.013 inches, preferably about 0.007 to 0.011 inches. It should be understood that the optimum differential depends in part on the physical charteristics of the spring material selected for the chuck. While any of a variety of spring metals may be used, particularly effective results have been achieved using a high-strength stainless spring steel having the following mechanical properties at room temperature when tested as a one-inch bar section: a 0.2% yield strength of 225,000 psi; an elongation of 12% (in 4D); and a hardness of 48 on the Rockwell C scale. Such a steel is commercially available under the designation "Custom 455" from Carpenter Technology Corporation, Redding, Pa., and other steels having similar properties may be available elsewhere.

The wedge-providing element or member 30 has an axial bore 33 aligned with the bore 21 of chuck 20. Like bore 21, bore 33 is only slightly larger in diameter than the outside diameter of bur 22. A differential of about 0.0002 to 0.0013 inches has been found suitable; therefore, where a handpiece designed for use with standard burs of a diameter within the range of 0.0626 to 0.0630 inches, the diameter of bores 33 and 21 should preferably fall within the range of about 0.0632 to 0.0639 inches.

Figure 4:
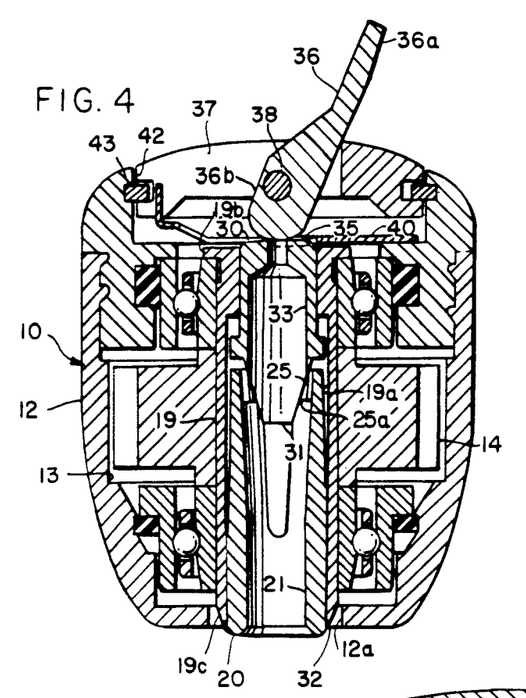
FIG. 4 is a vertical sectional view similar to FIG. 2 but showing the control lever in raised or extended position.

As shown in FIG. 2, the upper end of the wedge-providing member 30 projects upwardly from the open upper end 19b of bur tube 19 and provides an upwardly-facing bearing surface 35 disposed directly below a control lever 36 pivotally carried by disk-shaped cap or cover member 37. The lever includes a handle portion 36a, a cam portion 36b, and a transverse pivot shaft 38. In the preferred embodiment shown, the pivot shaft 38 has its horizontal axis substantially perpendicular to the vertical longitudinal axis of the bur tube and the chucking mechanism retained by it. It will be observed that lever portion 36a is considerably longer than cam portion 36b—preferably at least three times greater in length—so that a substantial mechanical advantage is produced when the lever is pivoted upwardly from its horizontal retracted position (FIG. 2) into its raised or extended position (FIG. 4).

When lowered, the control lever 36 is received and substantially concealed within a recess or slot 39 formed in the disk-shaped cover 37. The end of the handle portions of the retracted lever protrudes a slight distance radially outwardly beyond the outer surface of the handpiece's head although its radial extent does not exceed the full radius of that head (FIG. 2). The protrusion of the handle portion provides an undercut for catching the lever with a fingernail and commencing upward pivotal movement of the lever into the fully raised or extended position of FIG. 4.

Ideally, the lever is mounted so that its undersurface is spaced above bearing surface 35 of wedge member 30 when the lever is in its lowered or retracted position (FIG. 2). Such a relationship facilitates commencement of upward pivotal movement of the lever when chuck actuation is desired (because the first few degrees of pivotal movement do not involve contact with wedge member 30 and application of the substantial forces necessary to drive the wedge member downwardly to open the jaws of chuck 20) and also performs a protective function (since there is no risk that limited upward pivotal movement of the lever will cause bur release). A leaf spring 40 of developed shape is disposed beneath cover 37 and exerts an upward force against cam portion 36b of the lever to hold the lever in its lowered or retracted position. As shown most clearly in FIG. 3, the spring includes an arcuate upper portion 40a that bears against the cam surface of the lever, an annular portion 40b that extends about the protruding upper end of wedge member 30, and a hook portion 40c that extends upwardly and is received within the slot 39 in which the control lever is mounted. Spring 40 therefore exerts a force sufficient to hold the control lever in its lowered or retracted position until such time as the operator wishes to insert or remove a bur 22.

The disk-shaped cover 37 is mounted for rotation within upwardly-facing cavity 42 provided by head 12. A retaining ring 43 is received within opposing grooves 44 and 45 of the cover and head to hold the cover within the cavity without restraining cover rotation. Because the upstanding tongue 40c of the spring 40 is received within cover slot 39, the spring rotates along with the cover into whatever position is selected by the operator. A dentist's operating technique may make it desirable for the cover 37 and control lever 36 to be oriented in the positions depicted in FIG. 1; if another angular position of the lever would be more suitable, the dentist may rotate the cover one way or the other, as represented by arrows 46, into any desired position over a sweep of 360°.

To release the chuck 20, an operator simply pivots lever 36 into the raised position depicted in FIG. 4. As the handle portion 36a is raised, the cam portion 36b drives the wedge member 30 downwardly so that wedge portions 31 are expanded outwardly to permit insertion or removal of a bur 22. It is to be noted that when the control lever is fully raised, the substantial inwardly-directed forces exerted by the jaws 24 of the chuck generate a reactive force that tends to hold the lever in its raised position. More specifically, the jaws 24 exert a reactive camming force against wedge member 30 causing its surface 35 to bear upwardly against the arcuate surface of cam portion 36b of the lever and, since the lever has been pivoted more than 90° (i.e., beyond vertical), the control lever will tend to remain in the raised position of FIG. 4 unless it is intentionally pivoted downwardly into its lowered position of FIG. 2. Furthermore, during such downward pivotal movement, the spring force exerted by the jaws 24, and also the upward force exerted by leaf spring 40, urge the lever into its lowered position after it has passed a vertical mid point in its path of pivotal movement.

Figure 7:
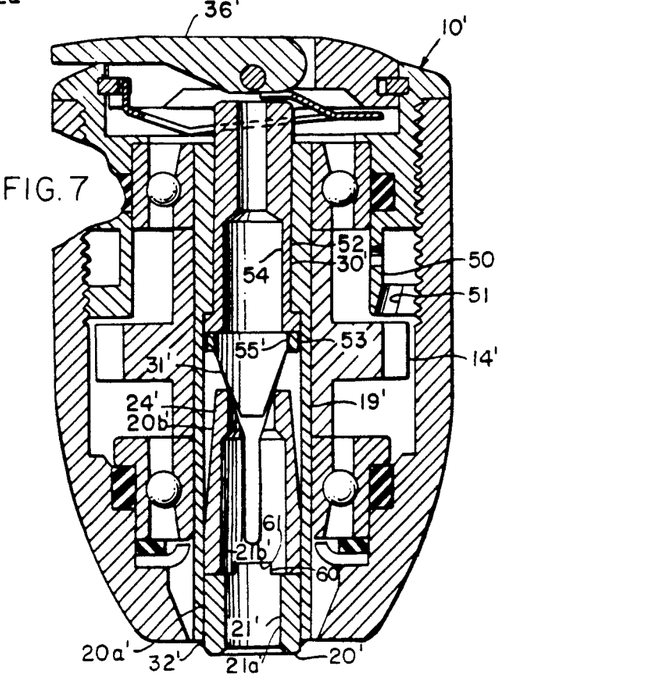
FIG. 7 is a vertical sectional view depicting another embodiment of the invention.

The handpiece 10' illustrated in FIG. 7 is basically similar to the one already described; however, it incorporates a stator 50 with orifices 51 for directing drive air downwardly in a general axial direction against the vanes of rotor 14'. Such a construction results in a handpiece having a relatively long bur or rotor tube 19'. The proportions of spring grip chuck 20' are similar to those of the previously-described chuck but a comparison of the drawings will reveal that wedge-providing member 30' is considerably longer for its diameter than wedge-providing member 30.

Unlike wedge member 30, wedge member 30' is composed of upper and lower sections 52 and 53, respectively. While the upper section has a bur-receiving bore 54 with a diameter only slightly greater than the diameter of a bur to be received therein, the bore 55 of the lower section 53 is shown to be substantially larger than either bore 54 of the upper section or bore 21' of chuck 20'. This permits slight displacement or tipping action of the lower section 53, without affecting the concentricity of bores 54 and 21' and without interfering with or obstructing insertion of the end of a bur into bore 54, when the jaws 24' of the chuck have been forced into their opened positions by upward pivotal movement of cam lever 36' and resulting downward movement of wedge member 30'. Stated differently, the spacing between the inner surface of bore 54 and the outer surface of a bur may be kept to a minimum without risk that the wedge portions 31' of the two-section member 30' might be forced out of alignment with bore 21' when the jaws of the chuck 20' are forced open. Should slight tipping action of lower section 53 occur under such circumstances, the relatively large inside diameter of bore 55 will still accommodate the bur, and the upper section 52 with its bur-piloting bore 54 will remain unaffected.

Also, unlike spring grip chuck 20, chuck 20' has lower and upper sections 20a' and 20b' that consist of separate pieces locked together against independent relative rotation by means of interfitting tongue 60 and recess 61. The bore 21a' of the lower section 20a' has a diameter only slightly greater than the outside diameter of a bur and therefore performs the piloting function indicated above. The lower section 21a' is secured by weld 32' to bur tube 19' and presets the tension of the jaws 24' in the same manner already described. However, because the chuck is formed in two sections, the piloting and gripping functions are divided with the piloting function being performed by the lower section 20a' and the gripping function being performed by the upper section 20b'. For that reason, bore 21b' of the upper section may be substantially larger than the bore 21a' of the lower section (as shown). Such a construction assures that the outward flexing of the pretensioned jaws into their fully open positions will not be accompanied by cross-sectional deformations of the lower section 20a' that might tend to reduce its piloting effectiveness.

While a two-piece chuck has been shown only in connection with the second embodiment of FIG. 7, it is believed apparent that such a construction may also be utilized with the embodiment of FIGS. 1–6. Conversely, the construction of FIG. 7 might, if desired, be provided with a one-piece chuck of the type shown and described in connection with the first embodiment.

Figure 8:
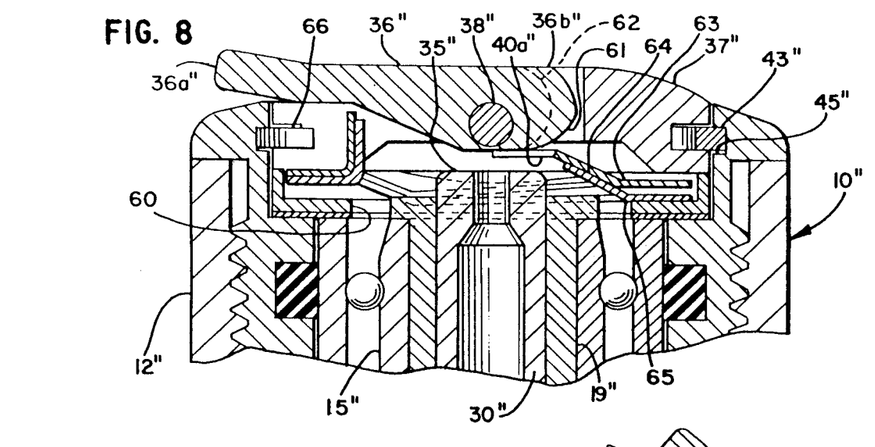
FIG. 8 is a fragmentary vertical sectional view showing the head of a handpiece constituting a third embodiment of the invention.
Figure 9:
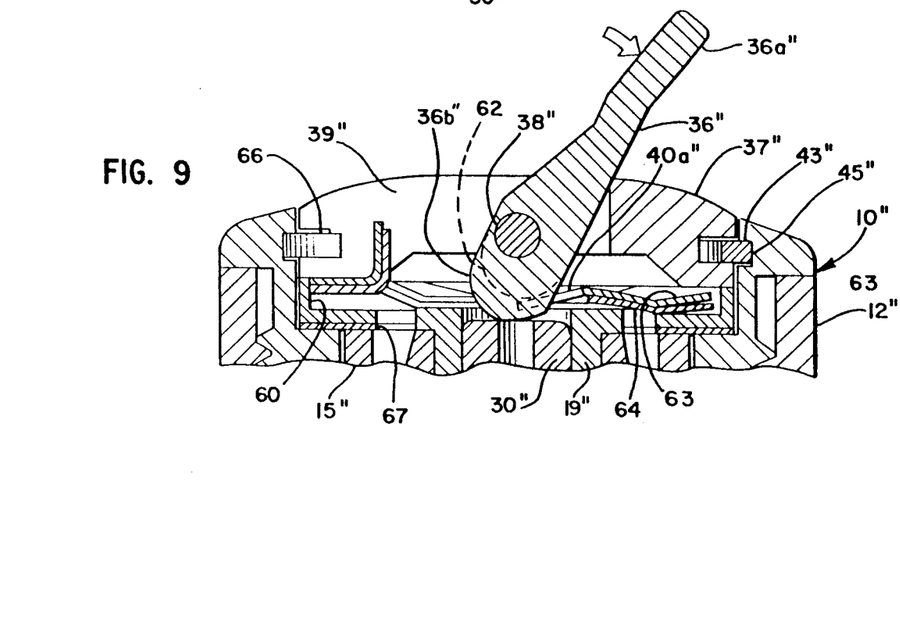
FIG. 9 is a vertical sectional view similar to FIG. 8 but showing the relationship of parts when the control lever of the handpiece is in raised position.
Figure 10:
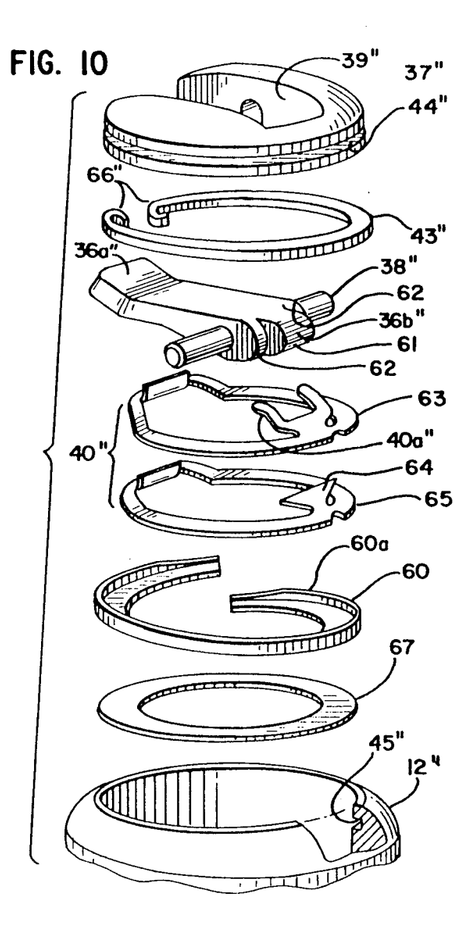
FIG. 10 is an exploded perspective view of the control lever and associated parts of the embodiment of FIGS. 8 and 9.

The embodiment depicted in FIGS. 8–10 is similar to the embodiments already described and utilizes either the one-piece chuck of FIGS. 1–6 or the two-piece chuck of FIG. 7. The differences in the third embodiment of FIGS. 8–10 relates to the removability of the disk-shaped cover 37", the spring means 60 for exerting a uniform force for holding the cover 37" and control lever 36" in any selected radial position of adjustment, and the structural and functional relationships between the lever 36", wedge-providing member 30", and spring means 40".

Like the handpieces already described, handpiece 10" includes a bur or rotor tube 19" that contains the spring chuck (not shown) and the wedge-providing member 30" for opening the spring jaws of that chuck in the same manner already described. The jaws are forced into open position when control lever 36" is raised to force its cam portion 36b" into engagement with the bearing surface 35" at the upper end of wedge-providing member 30". More specifically, cam portion 36" of the control lever has an arcuate camming surface 61 that engages bearing surface 35" when the handle portion 36a" is raised.

As shown most clearly in FIG. 10, the arcuate camming surface 61 is flanked by a pair of arcuate contacting surfaces 62. The arcuate contacting surfaces 62 are closer to the axis of transverse pivot shaft 38" than arcuate camming surface 61 and are in continuous engagement with the spring arms 40a" of annular upper leaf spring 63. The upward force exerted by spring arms 40a" is supplemented by arm 64 of lower annular leaf spring 65, the two leaf springs 63 and 65 together constituting the spring means 40" for urging control lever 36" into its normal retracted position (FIG. 8) or, when the control lever is pivoted upwardly more than 90°, for helping to hold the lever in its raised or extended position. As shown in FIG. 8, arm 64 of the lower spring member bears upwardly against the arm portion 40a" of the upper spring member 63. The double-spring arrangement is believed advantageous because it insures that sufficient force will be exerted for holding the lever in its fully raised or fully lowered positions while minimizing the risks of spring fatigue and possible failure.

Problems of spring fatigue are also eliminated or minimized, without reducing the effectiveness of control lever 36", by positioning spring-contacting surfaces 62 closer to the pivot axis of transverse shaft 38" than bearing surface 61. The extent of flexure of spring arms 40a" is therefore minimized without reducing the axial displacement of wedge-providing member 30" when the control lever 36" is shifted between its raised and lowered positions.

Although spring fingers 40a" remain in continuous engagement with arcuate contacting surfaces 62, spring means 40" makes only a minor contribution in holding control lever 36" in the raised position depicted in FIG. 9. As in the preceding embodiments, the primary force for holding the lever in such raised position is provided by the chuck which exerts a reactive upward force on wedge-providing member 30" and which in turn bears against the arcuate camming surface 61 of the control lever 36". Thus, the primary function of spring means 40" is to insure that the handle portion 36a" of the control lever will not lift, or be inadvertently lifted, into a partially raised position, as the handpiece is moved about and especially when it is being used in a cutting operation. It will be observed that when the control lever 36" is lowered, the bearing surface 35" of the wedge-providing member 30" is out of contact with the lever; hence, the only spring force serving to maintain the lever in its lowered position is that force exerted by spring means 40".

As in preceding embodiments, the head 12" of the handpiece is provided with an annular channel or groove 45" for receiving a retaining ring 43". However, in the embodiment of FIGS. 8-10, the spring ring 43" is C-shaped in configuration with hook portions at its spaced ends 66. The C-shaped spring is also received in an opposing groove 44" in disk-shaped cover 37". The C-shaped spring therefore functions to hold the cover in position within the head but, since its end portions 66 are accessible through the radial recess 39" of the cover when the control lever 36" is raised, or partially raised, an operator may, by means of any suitable tool capable of engaging and urging together the ends of C-shaped spring 43", retract the spring from the annular channel 45" of the head and thereby release the cover 37" for removal.

The disk-shaped cover may be rotated 360° within head 12" into any selected position, that is, into any position in which the control lever 36" assumes the radial position (when retracted) preferred by the handpiece operator. In the embodiment of FIGS. 8-10, the force or resistance for maintaining the cover and lever in such selected rotational position is provided by cup spring 60 shown most clearly in FIG. 10. The cup spring is essentially a single-turn helical compression spring with a smooth undersurface and an upwardly extending retaining/bearing rim 60a. The rim extends about and thereby confines leaf spring members 63 and 65. In addition, the rim engages the undersurface of cover 37" and, because the spring 60 is in a state of compression when the handpiece is assembled, a resistance of constant force is exerted against the cover to hold the cover in its selected position of rotation. Beneath the cup spring 60 is a smooth planar bearing ring 67. The bearing ring is intended to serve a protective function, particularly with respect to the antifriction ball bearings 15" directly beneath it, but such bearing ring 67 may be omitted, if desired.

While in the foregoing, embodiments of the invention have been disclosed in considerable detail for purposes of illustration, it will be understood by those skilled in the art that many of these details may be varied without departing from the spirit and scope of the invention.

I claim:

1. A dental handpiece having a head; a rotor tube disposed for rotation within said head; said rotor tube having upper and lower ends; a tubular spring chuck having an open-ended axial bore for receiving the shank of a dental bur; said chuck having a lower end portion fixed to said rotor tube and an upper end portion providing at least two spring jaws with arcuate, inwardly-facing bur-gripping edges; said spring jaws being normally disposed with said edges positioned for engaging and retaining the shank of a dental bur being capable of being flexed outwardly into opened positions for disengaging and releasing such a bur; chuck releasing means slidably disposed in the upper end of said rotor tube above said chuck for movement between raised and lowered positions; said chuck releasing means including wedge surfaces for engaging said jaws to urge the same apart into their opened positions when said chuck releasing means is shifted into its lowered position; and a control lever having an elongated handle portion and being mounted upon said head for pivotal movement of said handle portion about a transverse pivot axis between a retracted lowered position and an extended raised position; said control lever also including a cam portion engagable with said chuck releasing means for driving said chuck releasing means into its lowered position when said handle portion is pivoted into its raised position; said jaws when in untensioned condition having their bur-gripping edges spaced substantially closer than the diameter of the shank of a standard bur receivable therebetween and engaging said wedge surfaces to preset said jaws to exert inwardly directed forces against said wedge surfaces when said chuck releasing means is in its raised position and no bur is received by said chuck.

2. The handpiece of claim 1 in which said arcuate, bur-gripping edges of said jaws each has an inside radius of curvature substantially less than the radius of curvature of said bore of said chuck.

3. The handpiece of claim 1 in which said chuck releasing means includes a bearing surface and said cam portion includes an arcuate camming surface engable with said bearing surface when said control lever is extended.

4. The handpiece of claim 2 in which said transverse pivot axis of said control lever is located directly above said bearing surface of said chuck releasing means.

5. The handpiece of claim 4 in which said control lever has a pivotal range of more than 90°; said handle portion being disposed generally horizontally when said control lever is retracted and said head is oriented with the rotational axis of said rotor tube disposed vertically, whereby, said handle portion pivots beyond vertical when said control lever is shifted into its fully extended position.

6. The handpiece of claim 3 in which said jaws of said chuck exert an upward force on said chuck releasing means when said control lever is extended, thereby retaining said control lever in extended position, and said jaws in bur-releasing positions, until an overriding force is applied to retract said control lever.

7. The handpiece of claims 3, 5, or 6 in which spring means is located within said head and bears upwardly against said cam portion of said control lever for urging said control lever into its retracted position.

8. A dental handpiece having a head; a rotor tube disposed for rotation within said head; said rotor tube having upper and lower ends; a tubular spring chuck having an open-ended axial bore for receiving the shank of a dental bur; said chuck having a lower end portion fixed to said rotor tube and an upper end portion providing at least two spring jaws with arcuate, inwardly-facing, bur-gripping edges; said spring jaws being normally disposed with said edges positioned for engaging and retaining the shank of a dental bur but being capable of being flexed outwardly into opened positions for disengaging and releasing such a bur; chuck releasing means slidably disposed in the upper end of said rotor tube above said chuck for movement between raised and lowered positions; said chuck releasing means including wedge surfaces for engaging said jaws to urge the same apart into their opened positions when said chuck releasing means is shifted into its lowered position; and a control lever having an elongated handle portion and being mounted upon said head for pivotal movement of said handle portion about a pivot axis and over a pivotal range of more than 90° between a retracted position and an extended raised position; said control lever also including a cam portion engagable with said chuck releasing means for driving said chuck releasing means into its lowered position when said handle portion is pivoted into its raised position; said chuck releasing means including a bearing surface and said cam portion including an arcuate camming surface engagable with said bearing surface when said handle portion of said control lever is pivoted into its raised position; said pivot axis of said control lever being located directly above said bearing surface of said chuck releasing means; and said handle portion being disposed generally horizontally when said handle portion of said control lever is in its retracted lowered position and said head is oriented with the rotational axis of said rotor tube disposed vertically, whereby, said handle portion pivots beyond vertical when shifted into its fully extended raised position; said jaws of said chuck exerting an upward force on said chuck releasing means when said handle portion of said control lever is in its fully extended raised position to maintain said handle portion in said fully extended raised position and said jaws in said opened positions until an overriding force is applied to retract the handle portion of said control lever.

9. A dental handpiece having a head; a rotor tube disposed for rotation within said head; said rotor tube having upper and lower ends; a tubular spring chuck having an open-ended axial bore for receiving the shank of a dental bur; said chuck having a lower end portion fixed to said rotor tube and an upper end portion providing at least two spring jaws with arcuate, inwardly-facing, bur-gripping edges; said spring jaws being normally disposed with said edges positioned for engaging and retaining the shank of a dental bur but being capable of being flexed outwardly into opened positions for disengaging and releasing such a bur; chuck releasing means slidably disposed in the upper end of said rotor tube above said chuck for movement between raised and lowered positions; said chuck releasing means including wedge surfaces for engaging said jaws to urge the same apart into their opened positions when said chuck releasing means is shifted into its lowered position; and a control lever having an elongated handle portion and being mounted upon said head for pivotal movement of said handle portion about a pivot axis between a retracted lowered position and an extended raised position; said control lever also including a cam portion engagable with said chuck releasing means for driving said chuck releasing means into its lowered position when said handle portion is pivoted into its raised position; said chuck releasing means including a bearing surface and said cam portion including an arcuate camming surface engagable with said bearing surface when said handle portion of said control lever is pivoted into its raised position; spring means being located within said head and bearing upwardly against said cam portion of said control lever, when the handle portion thereof is lowered, to exert a spring force for maintaining said handle portion in said retracted lowered position; said cam portion of said control lever also including at least one arcuate contacting surface engaged by said spring means; said arcuate contacting surface being located substantially closer to said pivot axis than said arcuate camming surface.

10. A dental handpiece having a head; a rotor tube disposed for rotation within said head; said rotor tube having upper and lower ends; a tubular spring chuck having an open-ended axial bore for receiving the shank of a dental bur; said chuck having a lower end portion fixed to said rotor tube and an upper end portion providing at least two spring jaws with arcuate, inwardly-facing, bur-gripping edges; said spring jaws being normally disposed with said edges positioned for engaging and retaining the shank of a dental bur but being capable of being flexed outwardly into opened positions for disengaging and releasing such a bur; chuck releasing means slidably disposed in the upper end of said rotor tube above said chuck for movement between raised and lowered position; said chuck releasing means including wedge surfaces for engaging said jaws to urge the same apart into their opened positions when said chuck releasing means is shifted into its lowered position; and a control lever having an elongated handle portion and being mounted upon said head for pivotal movement of said handle portion about a pivot axis over a pivotal range of more than 90° between a retracted lowered position and an extended raised position; said control lever also including a cam portion engagable with said chuck releasing means for driving said chuck releasing means into its lowered position when said handle portion is pivoted into its raised position; said chuck releasing means including a bearing surface and said cam portion including an arcuate camming surface engagable with said bearing surface when said handle portion of said control lever is pivoted into its raised position; said pivot axis of said control lever being located directly above said bearing surface of said chuck releasing means; said handle portion being disposed generally horizontally when said handle portion of said control lever is in its retracted lowered position and said head is oriented with the rotational axis of said rotor tube disposed vertically, whereby, said handle portion pivots beyond vertical when shifted into its fully extended raised position; spring means being located within said head and bearing upwardly against said cam portion of said control lever, when the handle portion thereof is lowered, to exert a spring force for maintaining said handle portion in said retracted lowered position; said cam portion of said control lever also including at least one arcuate contacting surface engaged by said spring means; said arcuate contacting surface being located substantially closer to said pivot axis than said arcuate camming surface.

11. The handpiece of claim 9 or 10 in which two of said arcuate contacting surfaces are provided by said cam portion of said control lever, one on each side of said arcuate camming surface.

12. The handpiece of claim 9 or 10 in which said spring means comprises at least one annular leaf spring supported by said head beneath, and in engagement with, said arcuate contacting surface.

13. The handpiece of claim 12 in which a pair of said annular leaf springs is provided beneath said arcuate contacting surface.

14. A dental handpiece having a head; a rotor tube disposed for rotation within said head; said rotor tube having upper and lower ends; a tubular spring chuck having an open-ended axial bore for receiving the shank of a dental bur; said chuck having a lower end portion fixed to said rotor tube and an upper end portion providing at least two spring jaws with arcuate, inwardly-facing, bur-gripping edges; said spring jaws being normally disposed with said edges positioned for engaging and retaining the shank of a dental bur but being capable of being flexed outwardly into opened positions for disengaging and releasing such a bur; chuck releasing means slidably disposed in the upper end of said rotor tube above said chuck for movement between raised and lowered positions; said chuck releasing means including wedge surfaces for engaging said jaws to urge the same apart into their opened positions when said chuck releasing means is shifted into its lowered position; and a control lever having an elongated handle portion and being mounted upon said head for pivotal movement of said handle portion about a pivot axis between a retracted lowered position and an extended raised position; said control lever also including a cam portion engagable with said chuck releasing means for driving said chuck releasing means into its lowered position when said handle portion is pivoted into its raised position; said chuck releasing means having a downwardly-facing axial bore dimensioned to receive a portion of the shank of a dental bur; said chuck releasing means including separate upper and lower sections; said upper section being engagable by said cam portion of said control lever and said lower section providing said wedge surfaces engagable with said jaws of said chuck; the portion of said bore extending through said lower section of said chuck releasing means being substantially greater in diameter than the portion of said bore in said upper section thereof.

15. A dental handpiece having a head; a rotor tube disposed for rotation within said head; said rotor tube having upper and lower ends; a tubular spring chuck having an open-ended axial bore for receiving the shank of a dental bur; said chuck having a lower end portion fixed to said rotor tube and an upper end portion providing at least two spring jaws with arcuate, inwardly-facing, bur-gripping edges; said spring jaws being normally disposed with said edges positioned for engaging and retaining the shank of a dental bur but being capable of being flexed outwardly into opened positions for disengaging and releasing such a bur; chuck releasing means slidably disposed in the upper end of said rotor tube above said chuck for movement between raised and lowered positions; said chuck releasing means including wedge surfaces for engaging said jaws to urge the same apart into their opened positions when said chuck releasing means is shifted into its lowered position; and a control lever having an elongated handle portion and being mounted upon said head for pivotal movement of said handle portion about a pivot axis between a retracted lowered position and an extended raised position; said control lever also including a cam portion engagable with said chuck releasing means for driving said chuck releasing means into its lowered position when said handle portion is pivoted into its raised position; said upper end portion and said lower end portion of said chuck comprising separate upper and lower coaxial chuck sections; means connecting said upper and lower chuck sections against independent relative rotation within said rotor tube; said lower chuck section having its bore of smaller diameter than the bore of said upper chuck section when said jaws are flexed outwardly into bur-releasing positions.

16. A dental handpiece having a head; a rotor tube disposed for rotation within said head; said rotor tube having upper and lower ends; a tubular spring chuck having an open-ended axial bore for receiving the shank of a dental bur; said chuck having a lower end portion fixed to said rotor tube and an upper end portion providing at least two spring jaws with arcuate, inwardly-facing, bur-gripping edges; said spring jaws being normally disposed with said edges positioned for engaging and retaining the shank of a dental bur being capable of being flexed outwardly into opened positions for disengaging and releasing such a bur; chuck releasing means slidably disposed in the upper end of said rotor tube above said chuck for movement between raised and lowered positions; said chuck releasing means including wedge surfaces for engaging said jaws to urge the same apart into their opened positions when said chuck releasing means is shifted into its lowered position; and a control lever having an elongated handle portion and being mounted upon said head for pivotal movement of said handle portion about a transverse pivot axis between a retracted lowered position and an extended raised position; said control lever also including a cam portion engagable with said chuck releasing means for driving said chuck releasing means into its lowered position when said handle portion is pivoted into its raised position; said jaws when in untensioned condition having their bur-gripping edges spaced substantially closer than the diameter of the shank of a standard bur receivable therebetween and engaging said wedge surfaces to preset said jaws to exert inwardly directed forces against said wedge surfaces when said chuck releasing means is in its raised position and no bur is received by said chuck; said chuck releasing means including a bearing surface and a cam portion including an arcuate camming surface engagable with said bearing surface when said control lever is extended; spring means being located within said head and bearing upwardly against said cam portion of said control lever for urging said control lever into its retracted position; said cam portion of said control lever also including at least one arcuate contacting surface engaged by said spring means; said arcuate contacting surface being located substantially closer than said arcuate camming surface to said pivot axis.

17. The handpiece of claim 16 in which two of said arcuate contacting surfaces are provided by said cam portion of said control lever, one on each side of said arcuate camming surface.

18. The handpiece of claim 17 in which said spring means comprises at least one annular leaf spring supported by said head beneath, and in engagement with, said arcuate contacting surface.

19. The handpiece of claim 18 in which a pair of said annular leaf springs is provided beneath said arcuate contacting surface.

20. A dental handpiece having a head; a rotor tube disposed for rotation within said head; said rotor tube having upper and lower ends; a tubular spring chuck having an open-ended axial bore for receiving the shank of a dental bur; said chuck having a lower end portion fixed to said rotor tube and an upper end portion providing at least two spring jaws with arcuate, inwardly-facing bur-gripping edges; said spring jaws being normally disposed with said edges positioned for engaging and retaining the shank of a dental bur being capable of being flexed outwardly into opened positions for disengaging and releasing such a bur; chuck releasing means slidably disposed in the upper end of said rotor tube above said chuck for movement between raised and lowered positions; said chuck releasing means including wedge surfaces for engaging said jaws to urge the same apart into their opened positions when said chuck releasing means is shifted into its lowered position; and a control lever having an elongated handle portion and being mounted upon said head for pivotal movement of said handle portion about a transverse pivot axis between a retracted lowered position and an extended raised position; said control lever also including a cam portion engagable with said chuck releasing means for driving said chuck releasing means into its lowered position when said handle portion is pivoted into its raised position; said jaws when in untensioned condition having their bur-gripping edges spaced substantially closer than the diameter of the shank of a standard bur receivable therebetween and engaging said wedge surfaces to preset said jaws to exert inwardly directed forces against said wedge surfaces when said chuck releasing means is in its raised position and no bur is received by said chuck; said chuck releasing means having a downwardly-facing axial bore dimensioned to receive a portion of the shank of a dental bur.

21. The handpiece of claim 20 in which said chuck releasing means includes separate upper and lower sections; said upper section being engagable by said cam portion of said control lever and said lower section providing said wedge surfaces engagable with said jaws of said chuck; the portion of said bore extending through said lower section of said chuck releasing means being substantially greater in diameter than the portion of said bore in said upper section thereof.

22. A dental handpiece having a head; a disk-shaped cover rotatably mounted upon said head; a rotor tube having upper and lower ends and being disposed for rotation within said head; a tubular spring chuck having an open-ended axial bore for receiving the shank of a dental bur; said chuck having a lower end portion fixed to said rotor tube and an upper end portion providing a pair of spring jaws with arcuate, inwardly-facing, bur-gripping edges; said spring jaws being normally disposed with said edges positioned for engaging and retaining the shank of a dental bur but being capable of being flexed outwardly for disengaging and releasing such a bur; chuck releasing means slidably disposed in the upper end of said rotor tube above said chuck for movement between raised and lowered positions; said chuck releasing means including wedge surfaces for engaging said jaws to urge the same apart into their bur-releasing positions when said chuck releasing means is shifted into its lowered position; and a control lever mounted upon said disk-shaped cover for pivotal movement about a transverse pivot axis between retracted and extended positions; said control lever having an elongated handle portion and a relatively short cam portion on opposite sides of said transverse pivot axis; said handle portion being in a lowered position in a radially-extending recess provided by said cover when said control lever is retracted and being in a raised position extending away from said recess when said control lever is extended; said cam portion being engageable with said chuck releasing means for driving said chuck releasing means into its lowered position when said handle portion is raised to shift said control lever into its extended position; spring means being located within said head and bearing upwardly against said cam portion of said control lever for urging said control lever into its retracted position; said spring means being connected to said cover for rotation therewith and comprising at least one annular leaf spring supported by said head beneath said control lever and in contact with said cam portion thereof.

23. The handpiece of claim 22 in which a pair of said annular leaf springs is provided in contact with each other for engagement with said cam portion.

24. A dental handpiece having a head; a disk-shaped cover rotatably mounted upon said head; a rotor tube having upper and lower ends and being disposed for rotation within said head; a tubular spring chuck having an open-ended axial bore for receiving the shank of a dental bur; said chuck having a lower end portion fixed to said rotor tube and an upper end portion providing a pair of spring jaws with arcuate, inwardly-facing, bur-gripping edges; said spring jaws being normally disposed with said edges positioned for engaging and retaining the shank of a dental bur but being capable of being flexed outwardly for disengaging and releasing such a bur; chuck releasing means slidably disposed in the upper end of said rotor tube above said chuck for movement between raised and lowered positions; said chuck releasing means including wedge surfaces for engaging said jaws to urge the same apart into their bur-releasing positions when said chuck releasing means is shifted into its lowered position; and a control lever mounted upon said disk-shaped cover for pivotal movement about a transverse pivot axis between retracted and extended positions; said control lever having an elongated handle portion and a relatively short cam portion on opposite sides of said transverse pivot axis; said handle portion being in a lowered position in a radially-extending recess provided by said cover when said control lever is retracted and being in a raised position extending away from said recess when said control lever is extended; said cam portion being engagable with said chuck releasing means for driving said chuck releasing means into its lowered position when said handle portion is raised to shift said control lever into its extended position; spring means being located within said head and bearing upwardly against said cam portion of said control lever for urging said control lever into its retracted position; said spring means being connected to said cover for rotation therewith; and a single-turn helical compression spring being supported in said head and engaging said cover to provide a limited and predetermined extent of frictional resistance to rotation of said cover within said head.

25. The handpiece of claim 24 in which said single-turn compression spring is a cup spring having an upstanding retaining rim.

26. The handpiece of claim 25 in which a planar bearing ring is disposed between said cup spring.

27. A dental handpiece having a head; a disk-shaped cover rotatably mounted upon said head; a rotor tube having upper and lower ends and being disposed for rotation within said head; a tubular spring chuck having an open-ended axial bore for receiving the shank of a dental bur; said chuck having a lower end portion fixed to said rotor tube and an upper end portion providing a pair of spring jaws with arcuate, inwardly-facing, bur-gripping edges; said spring jaws being normally disposed with said edges positioned for engaging and retaining the shank of a dental bur but being capable of being flexed outwardly for disengaging and releasing such a bur; chuck releasing means slidably disposed in the upper end of said rotor tube above said chuck for movement between raised and lowered position; said chuck releasing means including wedge surfaces for engaging said jaws to urge the same apart into their bur-releasing positions when said chuck releasing means is shifted into its lowered position; and a control lever mounted upon said disk-shaped cover for pivotal movement about a transverse pivot axis between retracted and extended positions; said control lever having an elongated handle portion and a relatively short cam portion on opposite sides of said transverse pivot axis; said handle portion being in a lowered position in a radially-extending recess provided by said cover when said control lever is retracted and being in a raised position extending away from said recess when said control lever is extended; said cam portion being engagable with said chuck releasing means for driving said chuck releasing means into its lowered position when said handle portion is raised to shift said control lever into its extended position; said chuck releasing means including a bearing surface engagable by said cam portion when said control lever is pivoted into its extended position; said transverse pivot axis of said control lever being located directly above said bearing surface of said chuck releasing means; said control lever having a pivotal range of more than 90°; said handle portion being disposed generally horizontally when said control lever is retracted and said head is oriented with the rotational axis of said rotor tube disposed vertically, whereby, said handle portion pivots beyond vertical when said control lever is fully extended; said jaws of said chuck exerting an upward force on said chuck releasing means when said control lever is extended, thereby retaining said control lever in extended position, and said jaws in said bur-releasing positions, until an overriding force is applied to said handle portion to retract said control lever.

28. A dental handpiece having a head; a disk-shaped cover rotatably mounted upon said head; a rotor tube having upper and lower ends and being disposed for rotation within said head; a tubular spring chuck having an open-ended axial bore for receiving the shank of a dental bur; said chuck having a lower end portion fixed to said rotor tube and an upper end portion providing a pair of spring jaws with arcuate, inwardly-facing, bur-gripping edges; said spring jaws being normally disposed with said edges positioned for engaging and retaining the shank of a dental bur but being capable of being flexed outwardly for disengaging and releasing such a bur; chuck releasing means slidably disposed in the upper end of said rotor tube above said chuck for movement between raised and lowered positions; said chuck releasing means including wedge surfaces for engaging said jaws to urge the same apart into their bur-releasing positions when said chuck releasing means is shifted into its lowered position; and a control lever mounted upon said disk-shaped cover for pivotal movement about a transverse pivot axis between retracted and extended positions; said control lever having an elongated handle portion and a relatively short cam portion on opposite sides of said transverse pivot axis; said handle portion being in a lowered position in a radially-extending recess provided by said cover when said control lever is retracted and being in a raised position extending away from said recess when said control lever is extended; said cam portion being engagable with said chuck releasing means for driving said chuck releasing means into its lowered position when said handle portion is raised to shift said control lever into its extended position; said chuck releasing means having a downwardly-facing axial bore dimensioned to receive a portion of the shank of a dental bur and including separate upper and lower sections; said upper section being engagable by said cam portion of said control lever and said lower section providing said wedge surfaces engagable with said jaws of said chuck; the portion of said bore extending through said lower section of said chuck releasing means being substantially greater in diameter than the portion of said bore in said upper section thereof.

29. A dental handpiece having a head; a disk-shaped cover rotatably mounted upon said head; a rotor tube having upper and lower ends and being disposed for rotation within said head; a tubular spring chuck having an open-ended axial bore for receiving the shank of a dental bur; said chuck having a lower end portion fixed to said rotor tube and an upper end portion providing a pair of spring jaws with arcuate, inwardly-facing, bur-gripping edges; said spring jaws being normally disposed with said edges positioned for engaging and retaining the shank of a dental bur but being capable of being flexed outwardly for disengaging and releasing such a bur; chuck releasing means slidably disposed in the upper end of said rotor tube above said chuck for movement between raised and lowered positions; said chuck releasing means including wedge surfaces for engaging said jaws to urge the same apart into their bur-releasing positions when said chuck releasing means is shifted into its lowered position; and a control lever mounted upon said disk-shaped cover for pivotal movement about a transverse pivot axis between retracted and extended positions; said control lever having an elongated handle portion and a relatively short cam portion on opposite sides of said transverse pivot axis; said handle portion being in a lowered position in a radially-extending recess provided by said cover when said control lever is retracted and being in a raised position extending away from said recess when said control lever is extended; said cam portion being engagable with said chuck releasing means for driving said chuck releasing means into its lowered position when said handle portion is raised to shift said control lever into its extended position; said upper end portion and said lower end portion of said chuck comprising separate coaxial upper and lower chuck sections; means connecting said upper and lower chuck sections against independent relative rotation within said rotor tube; said lower chuck section having a bore of smaller diameter than the bore of said upper chuck section when said jaws are flexed outwardly into bur-releasing positions.

* * * * *